(12) United States Patent
Tour et al.

(10) Patent No.: US 8,992,881 B2
(45) Date of Patent: Mar. 31, 2015

(54) GRAPHENE NANORIBBONS PREPARED FROM CARBON NANOTUBES VIA ALKALI METAL EXPOSURE

(75) Inventors: James M. Tour, Bellaire, TX (US); Dmitry Kosynkin, Houston, TX (US)

(73) Assignee: William Marsh Rice University, Houston, TX (US)

( * ) Notice: Subject to any disclaimer, the term of this patent is extended or adjusted under 35 U.S.C. 154(b) by 519 days.

(21) Appl. No.: 13/378,528

(22) PCT Filed: Jun. 11, 2010

(86) PCT No.: PCT/US2010/038368
§ 371 (c)(1),
(2), (4) Date: Apr. 11, 2012

(87) PCT Pub. No.: WO2010/147860
PCT Pub. Date: Dec. 23, 2010

(65) Prior Publication Data
US 2012/0197051 A1     Aug. 2, 2012

Related U.S. Application Data

(60) Provisional application No. 61/187,130, filed on Jun. 15, 2009.

(51) Int. Cl.
*C01B 31/06*    (2006.01)
*C01B 31/04*    (2006.01)
(Continued)

(52) U.S. Cl.
CPC .............. *C01B 31/0446* (2013.01); *C07C 1/32* (2013.01); *C07C 15/20* (2013.01); *B82Y 30/00* (2013.01);
(Continued)

(58) Field of Classification Search
CPC .. C01B 31/04; C01B 31/028; C01B 31/0293; C01B 31/0286; C07C 15/20; C07C 1/32
USPC ....... 423/448, 445 B, DIG. 40; 977/742, 985, 977/896
See application file for complete search history.

(56) References Cited

U.S. PATENT DOCUMENTS

| 2008/0128688 A1 | 6/2008 | Pan et al. |
| 2009/0029221 A1 | 1/2009 | Goddard et al. |
| 2010/0105834 A1* | 4/2010 | Tour et al. ....................... 525/50 |

OTHER PUBLICATIONS

Huang, Bing, et al. "Making a field effect transistor on a single graphene nanoribbon by selective doping." Applied Physics Letters 91.25 (2007): 253122.*

(Continued)

*Primary Examiner* — Richard M Rump
(74) *Attorney, Agent, or Firm* — Winstead PC (57) ABSTRACT

In various embodiments, the present disclosure describes processes for preparing functionalized graphene nanoribbons from carbon nanotubes. In general, the processes include exposing a plurality of carbon nanotubes to an alkali metal source in the absence of a solvent and thereafter adding an electrophile to form functionalized graphene nanoribbons. Exposing the carbon nanotubes to an alkali metal source in the absence of a solvent, generally while being heated, results in opening of the carbon nanotubes substantially parallel to their longitudinal axis, which may occur in a spiralwise manner in an embodiment. The graphene nanoribbons of the present disclosure are functionalized on at least their edges and are substantially defect free. As a result, the functionalized graphene nanoribbons described herein display a very high electrical conductivity that is comparable to that of mechanically exfoliated graphene.

28 Claims, 6 Drawing Sheets

(51) Int. Cl.
*C07C 1/32* (2006.01)
*C07C 15/20* (2006.01)
*B82Y 30/00* (2011.01)
*B82Y 40/00* (2011.01)
*C01B 31/02* (2006.01)

(52) U.S. Cl.
CPC ............. *B82Y 40/00* (2013.01); *C01B 31/0206* (2013.01); *C01B 31/0469* (2013.01); *C01B 2204/06* (2013.01); *Y10S 977/896* (2013.01)
USPC ........................ 423/448; 252/378 R; 977/896

(56) References Cited

OTHER PUBLICATIONS

Yazami, Rachid, Heike Gabrisch, and Brent Fultz. "Self-organized carbon nanostrips with a new LiC10 structure derived from carbon nanotubes." The Journal of Chemical Physics 115.23 (2001): 10585-10588.*
Kosynkin et al. "Longitudnal unzipping of carbon nanotubes to form graphene nanoribbons." Nature Letters, Apr. 16, 2009, vol. 458, pp. 872-877.
Li, et al. "Oxygen-Driven Unzipping of Graphitic Materials." Physical Review Letters, May 5, 2006, vol. 96, pp. 1-4.
Sinitskii et al. "Kinetics of Diazonium Functionalization of Chemically Converted Graphene Nanoribbons." ACS Nano, Mar. 26, 2010, vol. 4, No. 4, pp. 1949-1954.
Sinitskii et al. "Electronic Transport in Monolayer Graphene Nanoribbons Produced by Chemical Unzipping of Carbon Nanotubes." Applied Physics Letters, Dec. 23, 2009, vol. 95, pp. 1-3.
Han et al. "Energy band-gap engineering of graphene nanoribbons." Phys. Rev. Lett. 98, 206805/1-206805/4 (2007).
Schniepp et al. "Functionalized Single Graphene Sheets Derived from Splitting Graphite Oxide." J. Phys. Chem. B 110, 8535-8539 (2006).
Chen et al. "Graphene nano-ribbon electronics." Physica E 40, 228-232 (2007).
Rollings et al. "Synthesis and characterization of atomically thin graphite films on a silicon carbide substrate." J. Phys. Chem. Solids 67, 2172-2177 (2006).
Li et al. "Chemically Derived, Ultrasmooth Graphene Nanoribbon Semiconductors." Science 319, 1229-1232 (2008).
Campos-Delgado et al. "Bulk Production of a New Form of sp2 Carbon: Crystalline Graphene Nanoribbons." Nano Lett. 8, 2773-2778 (2008).
Yang et al. "Two-dimensional graphene nanoribbons." J. Am. Chem. Soc. 130, 4216-4217 (2008).
International Preliminary Report on Patentability for PCT/US2010/038368, Mailed on Dec. 29, 2011.
International Search Report and Written Opinion for PCT/US2010/038368, Mailed on Aug. 13, 2010.
The State Intellectual Property Office of the Peoples Republic of China, Notice on the First Office Action, Nov. 8, 2013, Application No. 201080034953.X.
The Patent Office of the State Intellectual Property Office of the Peoples Republic of China, Decision on Rejection, Jun. 5, 2014, Application No. 201080034953.X.
Japan Patent Office, Notice of Rejection, Feb. 26, 2014, Japanese Patent Application No. 2012-516143.
Instituto Mexicano De La Propiedad Industrial, Communication of the Substantive Examination Report, May 29, 2014, Application No. MX/a/2011/013545.
Cano-Marquez, Abraham G., et al., "Ex-MWNTs: Graphene Sheets and Ribbons Produced by Lithium Intercalation and Exfoliation of Carbon Nanotubes", Nano Lett., vol. 9, No. 4, 2009, pp. 1527-1533.
Carruthers, W., "Some Modern Methods of Organic Synthesis", 2nd. Ed., 1978, pp. 442-445.

* cited by examiner

GRAPHENE NANORIBBONS PREPARED FROM CARBON NANOTUBES VIA ALKALI METAL EXPOSURE

CROSS-REFERENCE TO RELATED APPLICATIONS

This application claims priority to U.S. Provisional Patent Application 61/187,130, filed Jun. 15, 2009, which is incorporated by reference in its entirety herein. This application is also related to U.S. patent application Ser. No. 12/544,017, filed Aug. 19, 2009, which is also incorporated by reference in its entirety herein.

STATEMENT REGARDING FEDERALLY SPONSORED RESEARCH

This invention was made with Government support under grant number FA8650-05-D-5807, awarded by the Department of Defense; and grant number FA9550-09-1-0581, awarded by the Department of Defense. The Government has certain rights in the invention.

BACKGROUND

It is well known that graphite consists of many $sp^2$-hybridized carbon sheets stacked on top of one another. When graphite is exfoliated into a few-layer structure, the individual graphitic sheets are collectively referred to a material known as graphene. Graphene typically refers to a material having less than about 10 graphitic layers. The graphitic layers are characterized by a two-dimensional basal plane having a hexagonal lattice structure. In many cases, various edge and/or basal plane functionalities such as, for example, carboxylic acid groups, hydroxyl groups, epoxide groups and ketone groups are also present due to oxidation that either occurs natively in graphite or during exfoliation. Oxidative damage may also manifest itself in the form of defects (i.e., holes) in the basal plane.

Graphene nanoribbons are a special class of graphene, which are similarly characterized by a two-dimensional basal plane, but with a large aspect ratio of their length to their width. In this regard, graphene nanoribbons bear similarity to carbon nanotubes, which have a comparable aspect ratio and are defined by one or more layers of graphene sheets rolled up to form a cylinder. Graphene nanoribbons possess a number of useful properties, including, for example, beneficial electrical conductivity. Unlike carbon nanotubes, which can be metallic, semimetallic or semiconducting depending on their chiral geometry and diameter, the electrical properties of graphene nanoribbons are governed primarily by their width. For example, graphene nanoribbons less than about 10 nm wide are semiconductors, whereas similar graphene nanoribbons having a width greater than about 10 nm are metallic or semimetallic conductors. The edge configurations of graphene nanoribbons having an "armchair" or "zigzag" arrangement of carbon atoms, along with any edge functional groups, also may affect the transmission of electron carriers. Such "armchair" and "zigzag" arrangements are analogous to those defined in the carbon nanotube art. Ballistic charge transport in graphene and graphene nanoribbons drops markedly if the $sp^2$ network of the graphene basal plane is disrupted by even a relatively small number of defects.

Various methods for making graphene sheets are known, including, for example, adhesive tape exfoliation of individual graphene layers from graphite, chemical-based exfoliation of graphene layers from graphite, and chemical vapor deposition processes. Each method provides on the order of picogram quantities of graphene. Several lithographic and synthetic procedures have been developed for producing minuscule amounts of graphene nanoribbons. Microscopic quantities of graphene nanoribbons have been produced by partial encapsulation of carbon nanotubes in a polymer, followed by plasma etching to longitudinally cut the carbon nanotubes. Macroscopic quantities of graphene nanoribbons have been produced by a chemical vapor deposition process or by an oxidative process in concentrated acid.

In addition, multi-walled carbon nanotubes (MWNTs) have been non-selectively opened by intercalation and reaction with lithium in liquid ammonia solvent, resulting in longitudinal carbon nanotube opening to produce multilayered graphitic structures including partially opened MWNTs, graphene flakes, and graphene nanoribbons functionalized with hydrogen. Graphene nanoribbons prepared by these processes are typically characterized by multiple graphene layers with a kinked morphology and a defect-prone atomic structure having various oxygenated functionality, because the MWNT starting material has to be oxidatively damaged to provide sites for the lithium-ammonia reaction to occur. Although oxygenated functionality in graphene nanoribbons can be largely removed by subsequent reduction, defects in the graphene basal plane are not repaired by reduction, and the conductivity does not approach that of pristine graphene. While the lithium intercalation method is reductive and does not introduce oxygenated functionality into the graphene nanoribbons, defect-free graphene nanoribbons are not produced by this method due to the initial introduction of defects into the MWNTs, which are then carried forward into the graphene nanoribbon product.

In view of the foregoing, methods for preparing graphene nanoribbons having a substantially defect-free structure would be of considerable benefit in the art. Such defect-free graphene nanoribbons may demonstrate considerable utility in electronic, mechanical and many other applications. Ideally, such methods would be scalable to produce macroscopic amounts of the graphene nanoribbons.

SUMMARY

In various embodiments, processes for preparing graphene nanoribbons are described herein. In some embodiments, the processes include exposing a plurality of carbon nanotubes to an alkali metal source in the absence of a solvent, and after exposing, adding an electrophile to form functionalized graphene nanoribbons. Exposing opens the carbon nanotubes parallel to their longitudinal axis.

In some embodiments, the processes include exposing a plurality of multi-wall carbon nanotubes to a potassium metal source in the absence of a solvent, and after exposing, adding an electrophile to form functionalized graphene nanoribbons. Exposing opens the carbon nanotubes parallel to their longitudinal axis.

In still other various embodiments, functionalized graphene nanoribbons prepared by the processes described herein are disclosed. In some embodiments, the graphene nanoribbons are exfoliated, functionalized graphene nanoribbons. In other various embodiments, the graphene nanoribbons are defunctionalized graphene nanoribbons.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

The following definitions are set forth to aid in understanding of the various embodiments of the present disclosure. Terms in addition to those below are defined, as required, throughout the Detailed Description.

"Graphene nanoribbons," as defined herein, refer to, for example, single- or multiple layers of graphene that have an aspect ratio of greater than about 5, based on their length and their width. As used herein, a material having less than about 50 graphitic carbon layers will be considered to be graphene.

"Functionalized graphene nanoribbons," as defined herein, refer to, for example, graphene nanoribbons that are functionalized at their edges and/or in their basal plane with various organic functional groups, halogens or hydrogen. As shown hereinafter, the organic functional groups, halogens and hydrogen are introduced to the graphene nanoribbons by reaction with an electrophile.

"Longitudinal opening," as defined herein, refers to, for example, opening of carbon nanotubes substantially parallel to their longitudinal axis to form graphene nanoribbons. As used herein, the term "parallel" refers to an opening of the carbon nanotubes that does not bisect the carbon nanotube's longitudinal axis. In an embodiment, longitudinal opening may involve a relatively straight bond opening process along the sidewall of the carbon nanotube, paralleling but not crossing the longitudinal axis. In another embodiment, longitudinal opening may involve a predominantly spiralwise opening of the carbon nanotubes, again paralleling but not crossing the longitudinal axis.

"Alkali metal," as defined herein, refers to, for example, a metal from Group 1 of the periodic table (e.g., lithium, sodium, potassium, rubidium and cesium).

"Alkaline earth metal," as defined herein, refers to, for example, a metal from Group 2 of the periodic table, (e.g., beryllium, magnesium, calcium, strontium and barium).

"Transition metal," as defined here, refers to, for example, a metal from Groups 4-12 of the periodic table.

"Rare earth metal," as defined herein, refers to, for example, a metal from Group 3 of the periodic table (e.g., scandium or yttrium) or a metal from the f-block of the periodic table (e.g., atomic numbers 57-71). Rare earth metals are also commonly referred to as lanthanides.

"Multi-walled carbon nanotubes (MWNTs)," as used herein will be understood to be inclusive of double-walled carbon nanotubes, triple-walled carbon nanotubes and any carbon nanotubes having two or more walls.

In various embodiments, processes of the present disclosure include exposing a plurality of carbon nanotubes to an alkali metal source in the absence of a solvent, and after exposing, adding an electrophile to form functionalized graphene nanoribbons. Exposing opens the carbon nanotubes substantially parallel to their longitudinal axis. In some embodiments, the opening occurs in a predominantly spiralwise manner. In some embodiments, the alkali metal intercalates between the carbon nanotubes and thereafter reacts to affect their longitudinal opening. In some or other embodiments, after longitudinal opening, the electrophile quenches excess alkali metal and functionalizes the graphene nanoribbons with various organic functional groups, halogens or hydrogen.

In some embodiments, the alkali metal source is a molten alkali metal. In other embodiments, the alkali metal source is an alkali metal vapor. In some embodiments, the alkali metal vapor is produced from a molten alkali metal. In some embodiments, the alkali metal used in the present processes may be, for example, potassium, rubidium, cesium or a combination thereof. In some embodiments, the alkali metal is potassium or a mixture of potassium and another metal.

In some embodiments, the alkali metal is covalently bound to the graphene nanoribbons before the electrophile is added.

In some embodiments, the alkali metal is covalently bound to the edges of the graphene nanoribbons. In other embodiments, the alkali metal is covalently bound to both the edges and the basal plane of the graphene nanoribbons. In some embodiments, the electrophile displaces the alkali metal from the graphene nanoribbons and introduces a plurality of functional groups to form the functionalized graphene nanoribbons.

Without being bound by theory or mechanism, Applicants' hereinafter present a non-limiting mechanistic explanation of the formation of functionalized graphene nanoribbons by the present processes. Alkali metal atoms first intercalate between the carbon nanotubes to form a carbon nanotube intercalation compound. Similar alkali metal intercalation compounds are known in the art for graphite and for carbon nanotubes when the alkali metal is lithium. In the present processes, the carbon nanotube intercalation compound is heated, under which conditions the carbon nanotubes become longitudinally opened to produce a graphene nanoribbon. Subsequent quenching with an electrophile functionalizes the graphene nanoribbons. Applicants believe that under the present experimental conditions of heating, transient openings (but not permanent defects) are opened in the carbon nanotube sidewalls to allow penetration of the alkali metal into the carbon nanotubes. Upon alkali metal penetration into the carbon nanotubes. mechanical strain is introduced into the carbon nanotubes' sidewalls. Once a first alkali metal atom has penetrated the carbon nanotubes, further alkali metal penetration becomes easier, and a self-propagating crack, fostered by the mechanical strain, occurs parallel, nearly parallel or spiralwise relative to the carbon nanotubes' longitudinal axes until the carbon nanotubes are fully opened to a graphene nanoribbon structure. In embodiments in which multi-walled carbon nanotubes are converted to graphene nanoribbons, once the outermost carbon nanotube has been longitudinally opened, the interior carbon nanotubes then become susceptible to attack by the alkali metal.

Figure 1A:
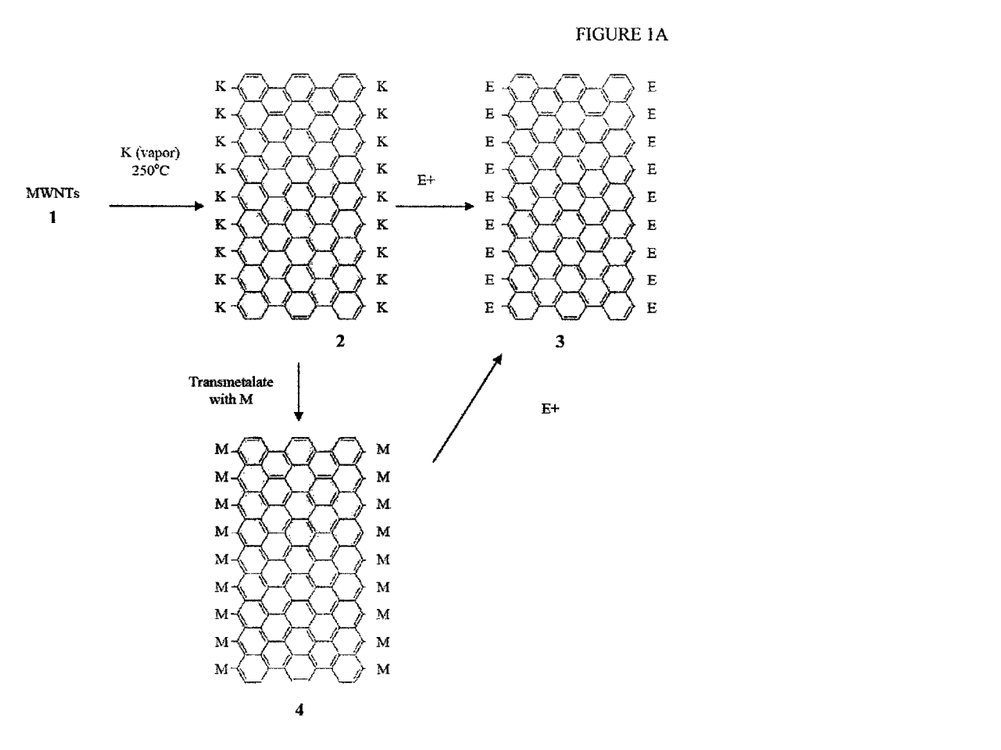
FIG. 1A shows a non-limiting reaction schematic illustrating the opening of multi-walled carbon nanotubes in the presence of potassium vapor, followed by quenching with an electrophile, to form functionalized graphene nanoribbons.

FIG. 1A shows a non-limiting reaction schematic illustrating the opening of multi-walled carbon nanotubes in the presence of potassium vapor, followed by quenching with an electrophile, to form functionalized graphene nanoribbons. In FIG. 1A, potassium is presented as an illustrative alkali metal and MWNTs as an illustrative carbon nanotube source. Other combinations of alkali metals and carbon nanotube sources lie within the spirit and scope of the present disclosure, and the embodiment of FIG. 1A should not be considered limiting. In the first step of FIG. 1A, MWNTs 1 are longitudinally opened in the presence of metallic potassium to produce organometallic graphene nanoribbon 2 having potassium covalently bound at least to the edge of the graphene nanoribbon. Organometallic graphene nanoribbon 2 is analogous to an aryl organometallic compound and displays comparable reactivity as a result. After formation of organometallic graphene nanoribbon 2, the organometallic intermediate is quenched with an electrophile E+ to form functionalized graphene nanoribbon 3.

Figure 1B:
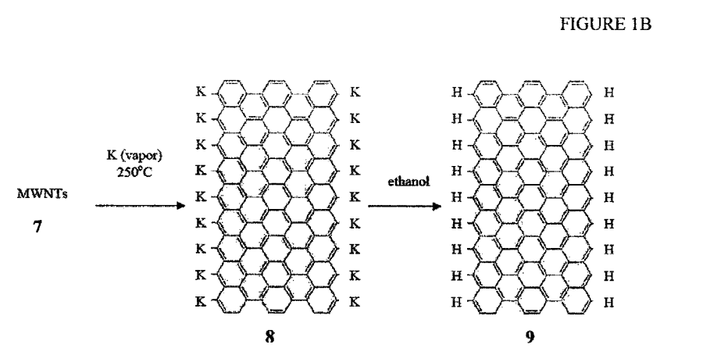
FIG. 1B shows a non-limiting reaction schematic illustrating the opening of multi-walled carbon nanotubes in the presence of potassium vapor, following by quenching with ethanol, to form hydrogen-functionalized graphene nanoribbons.

FIG. 1B presents a specific example of the general reaction illustrated in FIG. 1A. FIG. 1B shows a non-limiting reaction schematic illustrating the opening of multi-walled carbon nanotubes in the presence of potassium vapor, following by quenching with ethanol, to form hydrogen-functionalized graphene nanoribbons. In FIG. 1B, the electrophile is ethanol, a proton donor. As in FIG. 1A, MWNTs 7 are longitudinally opened in the presence of metallic potassium to produce organometallic graphene nanoribbon 8 having potassium covalently bound at least to the graphene nanoribbon's edge. After formation of organometallic graphene nanoribbon 8, the organometallic intermediate is quenched with ethanol to form hydrogen-functionalized graphene nanoribbon 9 having hydrogen moieties attached at least to its edge. Although not shown in FIGS. 1A and 1B, it should be noted that functionalized graphene nanoribbon 3 and hydrogen-functionalized graphene nanoribbon 9 may have functional groups (hydrogen) both on its edge, as illustrated in FIGS. 1A and 1B, and in its basal plane, given that alkali metals can reduce the graphene basal plane, as shown in the Birch reduction of carbon nanotubes. Only a single graphene nanoribbon layer has been shown in FIGS. 1A and 1B for purposes of clarity, although graphene nanoribbon stacks having multiple graphene layers are commonly produced by the methods described herein, as will be described hereinafter.

A number of electrophiles are capable of functionalizing the graphene nanoribbons to add various functional groups, halogens or hydrogen. As demonstrated in FIG. 1B, in some embodiments, the electrophile may be a proton donor, such as, for example, an alcohol or water. In other embodiments, the electrophile may be an organic halide (e.g., alkyl halide, aryl halide, benzylic halide, allylic halide, alkenyl halide, alkynyl halide or perfluoroalkyl halide) or a synthetic equivalent of an organic halide (e.g., a sulfonate ester). In still other embodiments, the electrophile may be a halogen (e.g., fluorine, chlorine, bromine or iodine), carbon dioxide, carboxylic acid, carboxylic ester, carboxylic acid chloride, carboxylic acid anhydride, aldehyde, ketone, enone, or nitrile. One of ordinary skill in the art will recognize the types of functional groups that are introduced when the aforesaid electrophiles are reacted with omanometallic reagents. One of ordinary skill in the art will further recognize that some of the electrophiles are more reactive with certain organometallic reagents than with others. That is, some electrophiles react more preferentially with certain organometallic reagents depending on the identity of the metal in the organometallic reagent.

In some embodiments, the electrophile may be a vinyl monomer such as, for example, styrene, acrylonitrile, methyl vinyl ketone, alkyl acrylates (e.g., methyl acrylate or ethyl acrylate), alkyl methacrylates (e.g., methyl methacrylate or ethyl methacrylate), and various combinations thereof. As one of ordinary skill in the art will recognize, vinyl monomers have a free vinyl group that is available for polymerization once the monomer becomes bound to the graphene nanoribbons. Thus, vinyl monomers represent one way in which polymer composites containing graphene nanoribbons covalently bound to the polymer may be formed. In some embodiments, the electrophile may be a ring-opening monomer such as, for example, a lactone or a lactam. Such ring-opening monomers represent another way in which polymer composites containing graphene nanoribbons covalently bound to the polymer may be formed.

Referring again to FIG. 1A, the organometallic graphene nanoribbon 2 may be transmetalated with a transmetalating species M to form transmetalated graphene nanoribbon 4. In the chemical arts, one of ordinary skill in the art will recognize that transmetalation is a common practice to alter the reactivity of a metal-carbon bond in an organometallic compound. For example, in organometallic graphene nanoribbon 2, the graphene-potassium bond makes the graphene a hard nucleophile. However, transmetalation to another metal such as, for example, zinc may make the graphene nanoribbon a softer nucleophile. As noted above, some electrophiles are more suitable for reaction with hard nucleophiles, whereas some electrophiles are more suitable for reaction with softer nucleophiles. Transmetalation is not strictly limited to metals, as non-metal transmetalating species such as, for example, boron may replace the potassium in organometallic graphene nanoribbon 2.

In some embodiments, processes of the present disclosure further include transmetalating the alkali metal with a transmetalating species before adding the electrophile. In some embodiments, the transmetalating species is an alkaline earth metal. In some embodiments, the transmetalating species is a transition metal or a rare earth metal. In some embodiments the transmetalating species is a non-metal such as, for example, boron. In some embodiments, the transmetalating species includes at least one metal such as, for example, magnesium, zinc, tin, palladium, copper, nickel or various combination thereof.

When the transmetalating species is magnesium, one of ordinary skill in the art will recognize the structural similarity and reactivity to that of a Grignard reagent. When the transmetalating species is zinc, one of ordinary skill in the art will recognize the structural similarity and reactivity to that of a Negishi reagent where the organozinc compound can be further reacted with a palladium or nickel catalyst and an organic electrophile to form a coupling product. When the transmetalating species is tin, one of ordinary skill in the art will recognize the structural similarity and reactivity to that of a Stille reagent of a Stille coupling. When the transmetalating species is copper, one of ordinary skill in the art will recognize the structural similarity and reactivity to that of a Sonogashira reagent of a Sonogashira coupling. When the transmetalating species is nickel, one of ordinary skill in the art will recognize the structural similarity and reactivity to that of a Fu cross-coupling sequence. When the transmetalating species is boron, one of ordinary skill in the art will recognize the structural similarity and reactivity to that of a boronic acid in Suzuki-type cross-couplings. Palladium or any other suitable catalytic metal may also catalyze further reactions of the graphene nanoribbons. Transmetalation may be particularly advantageous for forming carbon-carbon and carbon-heteroatom bonds to the graphene nanoribbons.

When bound to the graphene nanoribbons, some of the aforesaid transmetalating species may require a further catalyst in order to be reactive. For example, when the transmetalating species is boron, further catalysis by a palladium compound may be necessary to induce a Suzuki-type coupling. Likewise, when the transmetalating species is tin or copper, further catalysis by a palladium compound may be necessary to induce a Stille- or Sonogashira-type coupling, respectively.

In the present embodiments, exposing the carbon nanotubes to an alkali metal source takes place in the absence of a solvent. However, addition of the electrophile may take place either in the presence or in the absence of a solvent. In some embodiments, the electrophile is added in a solvent. In other embodiments, the electrophile is added neat. In some embodiments, the electrophile is a solvent in which the functionalized graphene nanoribbons are at least partially soluble.

In some embodiments of the present disclosure, the carbon nanotubes are multi-walled carbon nanotubes. Since multi-walled carbon nanotubes are significantly less expensive than single-walled carbon nanotubes, the present embodiments represent a relatively inexpensive route to prepare graphene nanoribbons. In some embodiments, the carbon nanotubes are substantially defect free, meaning that the functionalized graphene nanoribbons produced therefrom are substantially defect free in their basal plane. That is, in some embodiments, the functionalized graphene nanoribbons are substantially free from oxidative damage in their basal plane and have an electrical conductivity comparable to that of mechanically exfoliated graphene.

In some embodiments of the processes described herein, exposing the carbon nanotubes to the alkali metal source takes place at a temperature between about 50° C. and about 500° C. In other embodiments, exposing the carbon nanotubes to the alkali metal source takes place at a temperature between about 250° C. and about 300° C. In general, any temperature may be used that produces a molten alkali metal state and forms an alkali metal vapor. Temperatures higher than about 350° C. may represent safety concerns under the present experimental setup, as significant corrosion of glass occurs above about 350° C. upon exposure to molten potassium. Operations at greater than about 350° C. may be conducted by altering the present experimental setup to a quartz or metal alloy reactor vessel for reactivity and safety reasons.

As observed experimentally, the functionalized graphene nanoribbons of the present processes are typically not initially exfoliated into single- and few-layer functionalized graphene nanoribbon structures. Instead, the initially produced functionalized graphene nanoribbons have a trough-like structure resulting from incomplete exfoliation (for example, see FIG. 3A). Again without being bound by theory or mechanism, Applicants believe that the trough-like structure of non-exfoliated functionalized graphene nanoribbons is due to large interlayer van der Waals attractive forces that have not been overcome during longitudinal opening and functionalization. Rapid deintercalation of the alkali metal may also limit the entry of the electrophile or solvent into the interstitial space that would otherwise facilitate exfoliation.

Although some embodiments of the present processes produce non-exfoliated functionalized graphene nanoribbons, the functionalized graphene nanoribbons so produced may be exfoliated in further embodiments of the present processes to form single- and few-layer functionalized graphene nanoribbons. In some embodiments, the present processes further include exfoliating the graphene nanoribbons to form exfoliated, functionalized graphene nanoribbons. In some embodiments, exfoliated, functionalized graphene nanoribbons may include single- and few-layer (<10 carbon layer) functionalized graphene nanoribbons structures. In some other embodiments, exfoliated, functionalized graphene nanoribbons may have as many as about 50 carbon layers. In some embodiments, exfoliating involves exposing the functionalized graphene nanoribbons to a superacid solvent.

Superacid solvents suitable for practicing the various embodiments of the present disclosure include Brønsted superacids, Lewis superacids, and conjugate Brønsted-Lewis superacids. Brønsted superacids may include, for example, perchloric acid, chlorosulfonic acid, fluorosulfonic acid, trifluoromethanesulfonic acid, and higher perfluoroalkane sulfonic acids (e.g., $C_2F_5SO_3H$, $C_4F_9SO_3H$, $C_5F_{11}SO_3H$, $C_6F_{13}SO_3H$, and $C_8F_{17}SO_3H$). Lewis superacids may include, for example, antimony pentafluoride and arsenic pentafluoride. Brønsted-Lewis superacids may include sulfuric acids containing various concentrations of $SO_3$, also known as oleums or fuming sulfuric acid. Other Brønsted-Lewis superacids may include, for example, polyphosphoric acid-oleum mixtures, tetra(hydrogen sulfate)boric acid-sulfuric acid, fluorosulfuric acid-antimony pentafluoride ("magic acid"), fluorosulfuric acid-$SO_3$, fluorosulfuric acid-arsenic pentafluoride, fluorosulfonic acid-hydrogen fluoride-antimony pentafluoride, fluorosulfonic acid-antimony pentafluoride-sulfur trioxide, fluoroantimonic acid, and tetrafluoroboric acid. In some embodiments, superacid solvent is chlorosulfonic acid.

Processes of the present disclosure may further include spinning the superacid solution of functionalized graphene nanoribbons into fibers and conductive films. Spinning of graphene and graphene nanoribbons in superacid solutions is described in commonly assigned international patent application PCT/US2010/024574 which is incorporated herein by reference in its entirety. Alternatively, the functionalized graphene nanoribbons may be dissolved in a non-superacid solvent, either before or after exfoliation, and processed to form a fiber or a film. Illustrative solvents include, for example N,N-dimethylformamide, N-methylpyrrolidone and 1,2-dichlorobenzene.

Oxidation and reduction of graphite and graphene nanoribbons are described in commonly-assigned U.S. patent application Ser. No. 12/544,017 and international patent applications PCT/US2010/024574 and PCT/US2009/030498, each of which is incorporated herein by reference in its entirety. Although not typically preferred for electronics applications, some embodiments of the present disclosure further include oxidizing the functionalized graphene nanoribbons to form oxidized, functionalized graphene nanoribbons. Oxidation may be used to further tailor the solubility and ease of manipulation of the graphene nanoribbon structures. In some embodiments, oxidation may be conducted using any oxidant that is operable for oxidizing graphite. In some embodiments, oxidation may be conducted using methods described in the patent applications noted immediately hereinabove and incorporated herein by reference. In some embodiments, processes of the present disclosure further include reducing the oxidized, functionalized graphene nanoribbons. Reduction may remove some, most or substantially all of the oxidized functional groups introduced during oxidizing the functionalized graphene nanoribbons.

In some embodiments, the functionalized graphene nanoribbons may be further functionalized in their basal plane. Various methods for functionalizing graphene nanoribbons are described in U.S. patent application Ser. No. 12/544,017, which was incorporated by reference hereinabove. For example, in an embodiment, functionalized graphene nanoribbons may be further functionalized in their basal plane using a diazonium species.

In some embodiments, processes of the present disclosure further include defunctionalizing the functionalized graphene nanoribbons to form defunctionalized graphene nanoribbons. In some embodiments, defunctionalization is a thermal defunctionalization process. For example, in some embodiments, the functionalized graphene nanoribbons become defunctionalized above about 50° C. In some embodiments, the functionalized graphene nanoribbons become defunctionalized above about 100° C. In some embodiments, the functionalized graphene nanoribbons become defunctionalized above about 150° C. In some embodiments, the functionalized graphene nanoribbons become defunctionalized above about 200° C. In some embodiments, the functionalized graphene nanoribbons become defunctionalized above about 250° C. In some embodiments, the functionalized graphene nanoribbons become defunctionalized above about 300° C. In some embodiments, the functionalized graphene nanoribbons become defunctionalized above about 400° C. In some embodiments, the functionalized graphene nanoribbons become defunctionalized above about 500° C. Defunctionalization may be performed either in air, under inert atmosphere or under vacuum, for example. In some embodiments, defunctionalization may be performed in a solvent. Functionalization may be used to temporarily modify a physical property of the graphene nanoribbons while in the functionalized state, and a more desirable physical property may be restored in the graphene nanoribbons upon their being converted into a defunctionalized state. For example, functionalized graphene nanoribbons may be more soluble in solvents for electronic device applications or more dispersible in polymer composites. After the graphene nanoribbons are incorporated into the device or composite, the functional groups can be removed, if desired, to improve the electrical conductivity, for example.

In some embodiments, the processes of the present disclosure include exposing a plurality of multi-wall carbon nanotubes to a potassium metal source in the absence of a solvent, and after exposing, adding an electrophile to form functionalized graphene nanoribbons. Exposing opens the carbon nanotubes parallel to their longitudinal axis. In some embodiments, the opening occurs in a predominantly spiralwise manner about the longitudinal axis.

There are many potential uses for the various graphene nanoribbon compositions disclosed herein. Illustrative uses of the present compositions include, for example, additives for composite materials, filters for removing particulates, filters for removing dissolved salts (ion-exchange filters), filters for removing dissolved organic compounds, membranes for gas separation, materials for gas sequestration, additives for elastomeric materials to prevent explosive decompression, additives for drilling fluids, nanoreporters for oilfield operations, production of films, wound care agents and drug delivery agents for compounds that are poorly soluble or insoluble in water. In addition, the present graphene nanoribbon compositions are conductive and may be used, for example, in electronic devices, conductive and semiconductive films, electromagnetic shielding materials, controlled permittivity composites, batteries, and supercapacitors.

The present graphene nanoribbon compositions are believed to be particularly advantageous for applications relying on mechanical strength such as, for example, polymer composites. The presence of holes or other defects in the graphene nanoribbon's basal plane may detrimentally impact the tensile strength or gas impermeability. Such defects are eliminated or significantly minimized in the present graphene nanoribbon compositions.

In wound care applications, the graphene nanoribbons may be grafted or bonded to at least one anti-microbial agent. Such grafted graphene nanoribbon compositions may be included as part of a wound dressing to advantageously improve infection suppression, provide odor control and inhibit lipophilic toxins from entering the wound. For example, in a non-limiting embodiment, graphene nanoribbons that have been grafted or bonded to at least one anti-microbial agent may be added to ordinary gauze.

Water-soluble graphene nanoribbons may be prepared by attaching a plurality of polymer chains or small molecules thereto. Suitable polymers for conferring water solubility may include, for example, polyethylene glycol (PEG), polypropylene glycol, polyethylene imine (PEI), PEG-PEI block copolymers, polyvinyl pyrrolidone (PVP), polyvinyl alcohol (PVA), polyacrylic acid, dextrose, starch, pectin, agarose, and other polysaccharides. Suitable small molecules for conferring water solubility include, for example, 2-aminoethanesulfonic acid. Other molecules may also be used to modify the solubility of the graphene nanoribbons to alter their ion affinity and improve their biocompatibility, for example. By way of non-limiting example, targeting moieties such as, for example, folate, estrogens, epidermal growth factor (EGF) and aptamers may be attached to the graphene nanoribbons to improve their interaction with appropriate cellular receptors.

Chemical modification of the graphene nanoribbons can also make these compositions suitable for selective binding to cells expressing target receptors from diverse cellular dispersions or other biological fluids. Such modified graphene nanoribbon compositions may be fabricated into selective cellular filters or active elements of cellular and chemical sensors. For example, graphene nanoribbons functionalized with antibodies to influenza virus (or any other pathogen) and connecting two conductive leads (i.e., electrode terminals) will change impedance upon antigen binding. The resulting change in electrical properties enables the use of the functionalized graphene nanoribbons in sensors for diagnostic testing of biological fluids.

Water-soluble graphene nanoribbon compositions such as those described above may be exploited for sequestration of water-insoluble drugs for drug delivery applications. For example, in an embodiment, paclitaxel may be incorporated in a water-based formulation using water soluble graphene nanoribbons containing a plurality of polymer chains. Sequestration of paclitaxel and other drugs within the polymer chains of related carbon nanotube compositions have been described in commonly-assigned PCT publications WO 2008/18960 and WO 2009/070380, each of which is incorporated herein by reference. The amount of the water-soluble graphene nanoribbons sufficient to provide acceptable solubility of paclitaxel or other drugs may be dramatically lower than surfactants, Cremophor or liposomes typically used for the same purpose. Therefore, advantageous toxicity improvement is possible using the water-soluble graphene nanoribbon compositions of the present disclosure as a drug delivery vehicle.

EXPERIMENTAL EXAMPLES

The following examples are provided to more fully illustrate some of the embodiments disclosed hereinabove. It should be appreciated by those of ordinary skill in the art that the methods disclosed in the examples that follow represent techniques that constitute illustrative modes for practice of the disclosure. Those of ordinary skill in the art should, in light of the present disclosure, appreciate that many changes can be made in the specific embodiments that are disclosed and still obtain a like or similar result without departing from the spirit and scope of the disclosure.

Example 1

Synthesis of Functionalized Graphene Nanoribbons Using Potassium Vapor

MWNTs (1.00 g) and potassium metal pieces (3.00 g) were placed in a 50 mL Pyrex ampoule that was then evacuated and sealed with a torch (CAUTION: Potassium metal is highly reactive and appropriate precautions should be taken.). The potassium metal was melted at 250° C., and the reaction mixture was kept in a furnace at 250° C. for 14 hr. The heated ampoule contained a golden-bronze potassium intercalation compound and silvery droplets of unreacted potassium metal. After heating, the ampoule was cooled to room temperature and opened in a dry box or nitrogen-filled glove bag, and 20 mL of ethyl ether was then added. Ethanol (20 mL) was then added slowly into the ethyl ether suspension. Ethanol addition was accompanied by some bubbling from hydrogen evolution and heat release. The product was then collected on a PTFE membrane (0.45 μm) and washed successively with ethanol (20 mL), water (20 mL), ethanol (10 mL), and ether (30 mL). Thereafter, the product was dried in vacuum to give hydrogen-functionalized graphene nanoribbons as a black, fibrillar powder (1.00 g).

Example 2

Exfoliation of Functionalized Graphene Nanoribbons Using Chlorosulfonic Acid

The product of Example 1 (10 mg) was dispersed in chlorosulfonic acid (15 mL) using mild bath sonication from an ultrasonic jewelry cleaner (Cole-Parmer EW-08849-00) for 24 hours (CAUTION: Chlorosulfonic acid is a corrosive liquid and appropriate precautions should be taken.). Afterward, the mixture was quenched by pouring into 50 mL of ice, and the resulting suspension was filtered through a PTFE membrane (0.45 μm). The filter cake was dried under vacuum, and the resulting black powder was then dispersed in DMF with mild bath sonication for 15 minutes.

Example 3

Characterization of Functionalized Graphene Nanoribbons

Figure 2A:
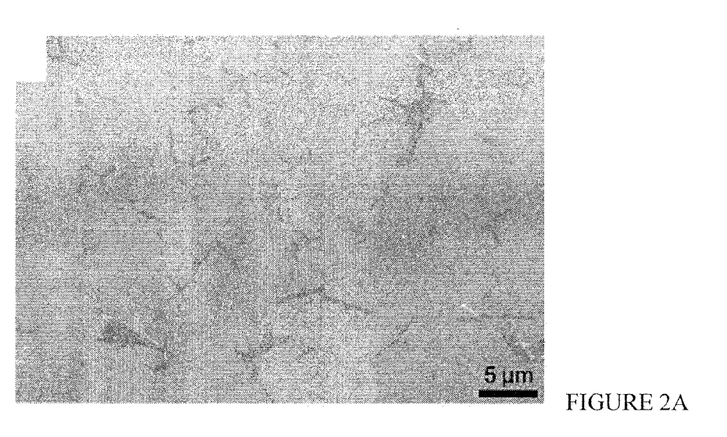
FIGS. 2A-2D show illustrative SEM images of functionalized graphene nanoribbons after exfoliation.
Figure 2B:
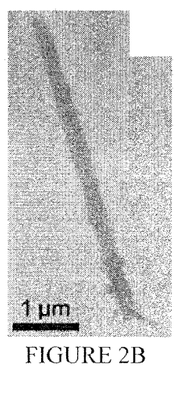
Figure 2C:
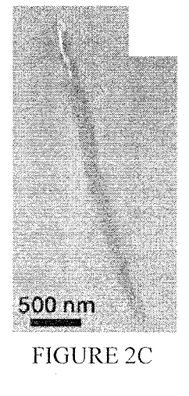
Figure 2D:
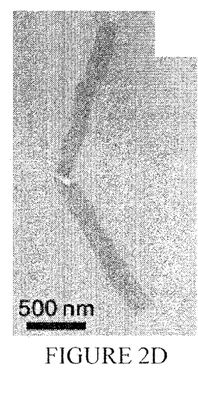
Figure 3A:
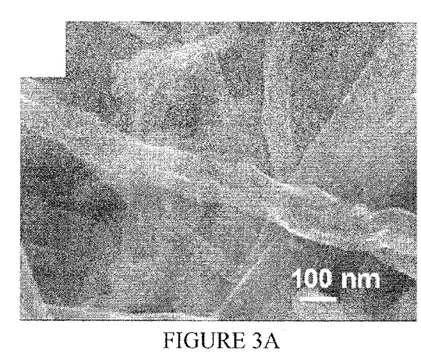
FIGS. 3A and 3B show illustrative SEM images of functionalized graphene nanoribbons prior to exfoliation.
Figure 3B:
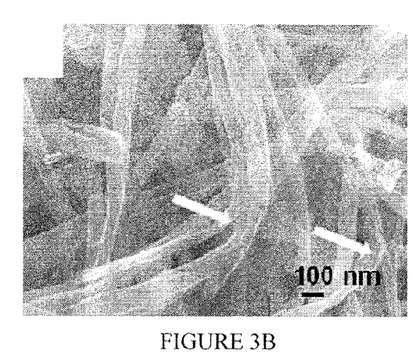

Scanning electron microscopy (SEM), transmission electronic microscopy (TEM) and atomic force microscopy (AFM) were used to image the functionalized graphene nanoribbons. FIGS. 2A-2D show illustrative SEM images of functionalized graphene nanoribbons after exfoliation. As shown in FIG. 2A, the functionalized graphene nanoribbons had widths ranging from ~130-250 nm and lengths ranging from ~1-5 μm. Magnified images of the functionalized graphene nanoribbons are shown in FIGS. 2B-2D. The SEM images of FIGS. 2B-2D showed that the functionalized graphene nanoribbons had a more ragged edge appearance than oxidized graphene nanoribbons produced by oxidative cleavage using $KMnO_4$ (see U.S. patent application Ser. No. 12/544,017). FIGS. 3A and 3B show illustrative SEM images of functionalized graphene nanoribbons prior to exfoliation. FIG. 3A illustrates substantial curling in the graphene nanoribbons prior to exfoliation. FIG. 3B shows that the functionalized graphene nanoribbons easily bend, unlike the multi-walled carbon nanotube starting material.

Figure 4:
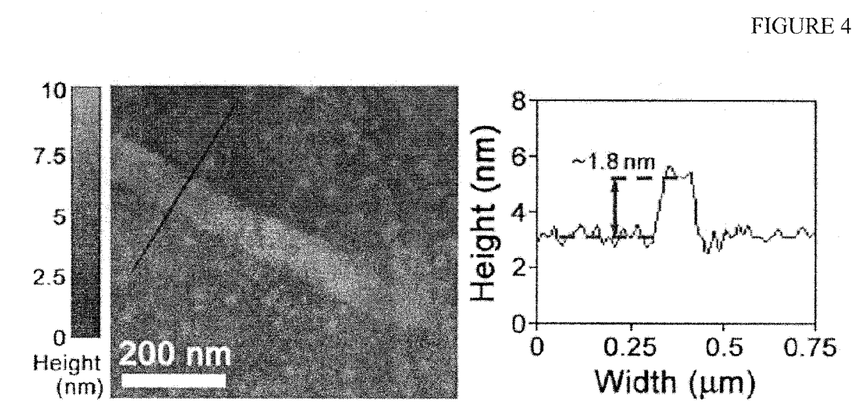
FIG. 4 shows an illustrative AFM image and height profile of functionalized graphene nanoribbons.
Figure 5A:
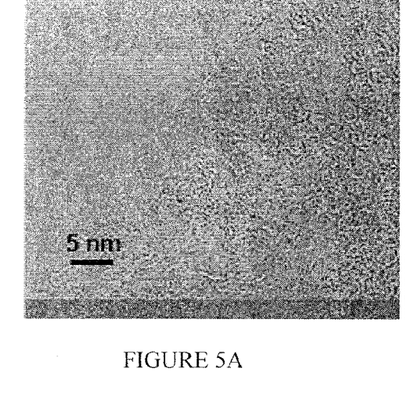
FIGS. 5A and 5B show illustrative TEM images of functionalized graphene nanoribbons.
Figure 5B:
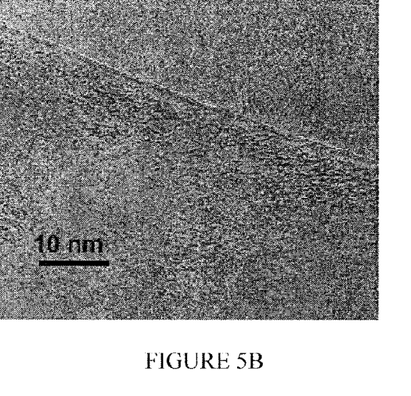

FIG. 4 shows an illustrative AFM image and height profile of functionalized graphene nanoribbons. The AFM height profile in FIG. 3 indicated a thickness of 1.8 nm, which is indicative of a functionalized graphene nanoribbon bilayer. The thickness of a single graphene sheet is generally considered to lie in the range of about 0.7 nm to about 1 nm. FIGS. 5A and 5B show illustrative TEM images of functionalized graphene nanoribbons.

Figure 6:
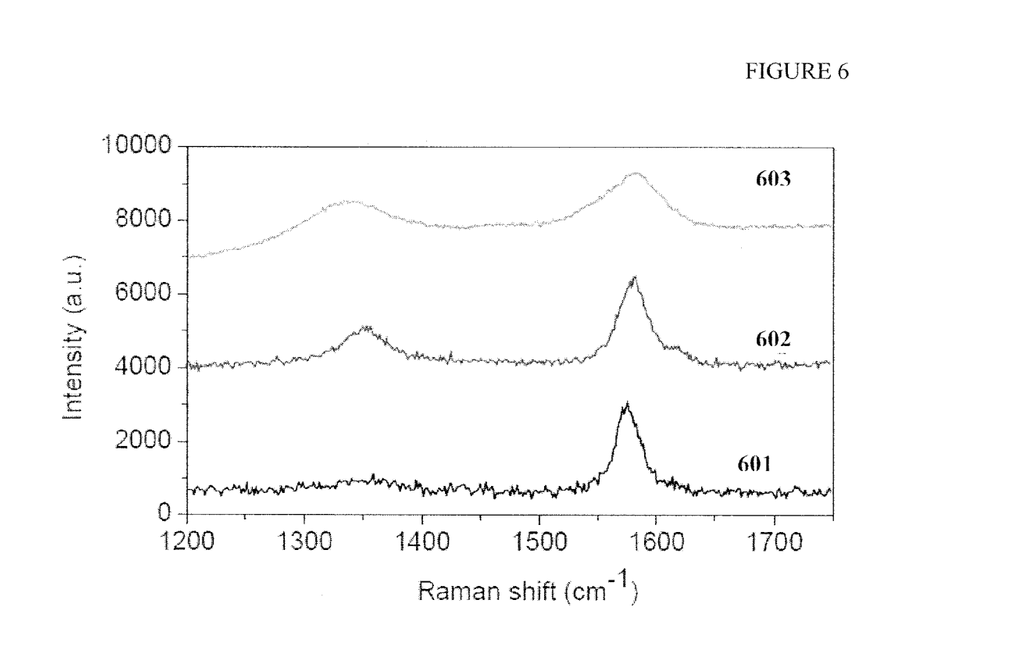
FIG. 6 shows illustrative Raman spectra of functionalized graphene nanoribbons before and after exfoliation in comparison to that of multi-walled carbon nanotubes.

FIG. 6 shows illustrative Raman spectra of functionalized graphene nanoribbons before and after exfoliation in comparison to multi-walled carbon nanotubes. The D/G band ratio of the Raman spectrum was increased over that of the carbon nanotube starting material, which is indicative of the relative lack of $sp^3$ carbons in the graphene lattice. Graphene basal plane defects are typically characterized by an increased proportion of $sp^3$ carbons. In FIG. 6, curve 601 shows the carbon nanotube starting material. Curve 602 shows the functionalized graphene nanoribbons before exfoliation, and curve 603 shows the functionalized graphene nanoribbons after exfoliation.

Figure 7:
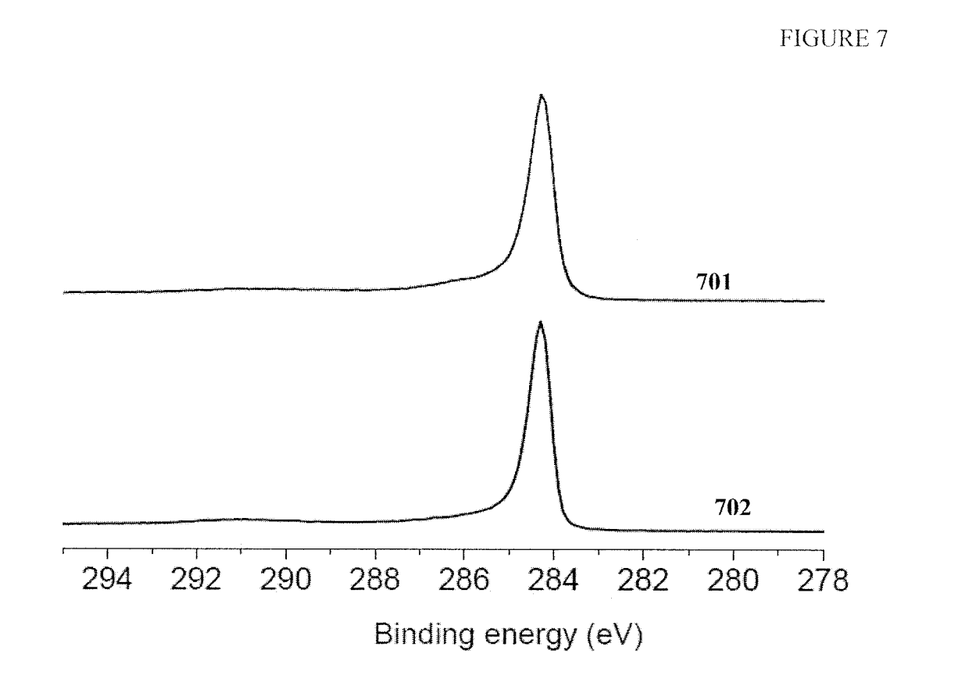
FIG. 7 shows an illustrative high resolution C1s XPS spectrum of functionalized graphene nanoribbons in comparison to that of multi-walled carbon nanotubes.

To further investigate the increased intensity of the D band, X-Ray photoelectron spectroscopy (XPS) was performed to determine if the increased intensity was due to oxidation. FIG. 7 shows an illustrative high resolution C1s XPS spectrum of functionalized graphene nanoribbons in comparison to that of multi-walled carbon nanotubes. Curve 701 shows the high resolution C1s XPS spectrum of functionalized graphene nanoribbons, and curve 702 shows that of the starting multi-walled carbon nanotubes. As shown in the XPS spectra, no signals were observed at either 286 eV (C—O) or 287 (C=O). Since the functionalized graphene nanoribbons lacked oxygen functionality, it can be concluded that they were not oxidized by the present processes. Hence, the increased D/G ratio is likely due to emergent edge carbons in the functionalized graphene nanoribbons.

Example 4

Electrical Property Measurements of Functionalized Graphene Nanoribbons

Figure 8:
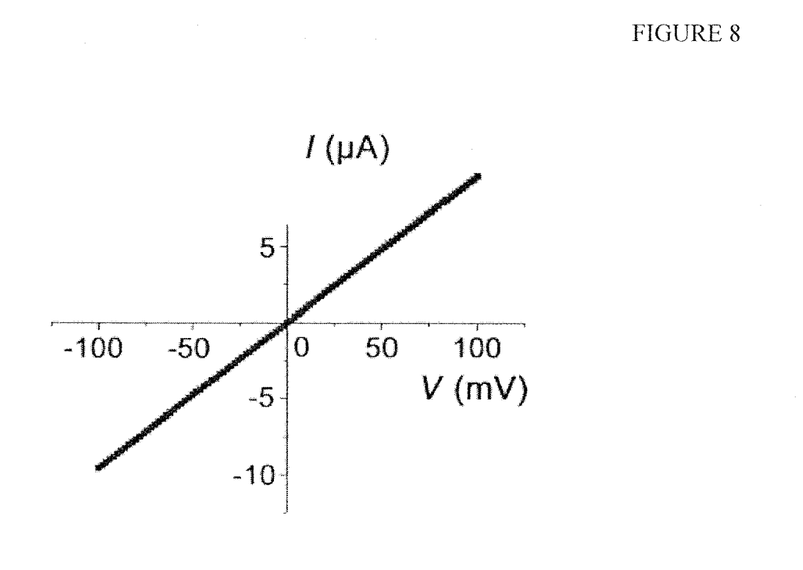
FIG. 8 shows an illustrative current versus voltage plot for a 3.8 nm thick functionalized graphene nanoribbon stack in an electronic device.

To investigate the electrical properties of the functionalized graphene nanoribbons, several electronic devices were constructed on an $Si/SiO_2$ substrate (for details, see U.S. patent application Ser. No. 12/544,017). Hydrogen-terminated graphene nanoribbons from Example 1 were used. The thicknesses of the functionalized graphene nanoribbons ranged from 3.5-5 nm in thickness, indicative of a several-layer thick stack of functionalized graphene nanoribbons. FIG. 8 shows an illustrative current versus voltage plot for a 3.8 nm thick functionalized graphene nanoribbon stack in an electronic device. The measured conductivities ranged from ~70,000 to ~90,000 S/m, which is comparable to that of mechanically exfoliated graphene. Only a very small gate effect was observed in the functionalized graphene nanoribbons, most likely due to the number of layers in the functionalized graphene nanoribbon stacks.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. A process for preparing graphene nanoribbons, said process comprising:
exposing a plurality of carbon nanotubes to an alkali metal source in the absence of a solvent, wherein the alkali metal source comprises an alkali metal vapor;
wherein exposing opens the carbon nanotubes parallel to their longitudinal axis; and
after exposing, adding an electrophile to form functionalized graphene nanoribbons.

2. The process of claim 1, wherein the alkali metal source comprises a molten alkali metal.

3. The process of claim 1, wherein the alkali metal source comprises an alkali metal selected from the group consisting of potassium, rubidium, cesium and combinations thereof.

4. The process of claim 3, wherein the alkali metal comprises potassium.

5. The process of claim 3, wherein the alkali metal is covalently bound to the graphene nanoribbons before the electrophile is added.

6. The process of claim 5, wherein the electrophile displaces the alkali metal from the graphene nanoribbons and introduces a plurality of functional groups to the functionalized graphene nanoribbons.

7. The process of claim 5, further comprising:
transmetalating the alkali metal with a transmetalating species before adding the electrophile;
wherein the transmetalating species comprises at least one element selected from the group consisting of boron, an alkaline earth metal, a transition metal, a rare earth metal, and combinations thereof.

8. The process of claim 7, wherein the transmetalating species comprises at least one element selected from the group consisting of magnesium, zinc, tin, palladium, copper, nickel, and combinations thereof.

9. The process of claim 1, wherein exposing takes place at a temperature between 50° C. and 500° C.

10. The process of claim 9, wherein exposing takes place at a temperature between about 250° C. and 300° C.

11. The process of claim 1, wherein the carbon nanotubes comprise multi-walled carbon nanotubes.

12. The process of claim 1, wherein the electrophile is selected from the group consisting of water, alcohols, organic halides and synthetic equivalents thereof, aldehydes, ketones, carboxylic acids, carboxylic esters, carboxylic acid chlorides, carboxylic acid anhydrides, enones, nitriles, carbon dioxide, halogens, vinyl monomers, ring-opening monomers and combinations thereof.

13. The process of claim 12, wherein the vinyl monomers are selected from the group consisting of styrene, acrylonitrile, methyl vinyl ketone, alkyl acrylates, alkyl methacrylates, and combinations thereof.

14. The process of claim 1, wherein the electrophile is added in a solvent.

15. The process of claim 1, wherein the electrophile is added neat.

16. The process of claim 1, further comprising:
exfoliating the functionalized graphene nanoribbons to form exfoliated, functionalized graphene nanoribbons.

17. The process of claim 16, wherein exfoliating comprises exposing the functionalized graphene nanoribbons to a superacid solvent.

18. The process of claim 1, further comprising:
oxidizing the functionalized graphene nanoribbons to form oxidized, functionalized graphene nanoribbons.

19. The process of claim 1, further comprising:
defunctionalizing the functionalized graphene nanoribbons to form defunctionalized graphene nanoribbons.

20. The process of claim 19, wherein defunctionalizing comprises a thermal defunctionalization process.

21. A process for preparing graphene nanoribbons, said process comprising:
exposing a plurality of multi-walled carbon nanotubes to a potassium metal source in the absence of a solvent, wherein the potassium metal source comprises potassium metal vapor;
wherein exposing opens the multi-walled carbon nanotubes parallel to their longitudinal axis; and
after exposing, adding an electrophile to form functionalized graphene nanoribbons.

22. The process of claim 21, wherein the potassium metal source comprises molten potassium metal.

23. The process of claim 21, wherein exposing takes place at a temperature between 50° C. and 500° C.

24. The process of claim 23, wherein exposing takes place at a temperature between 250° C. and 300° C.

25. The process of claim 21, wherein the electrophile is selected from the group consisting of water, alcohols, organic halides and synthetic equivalents thereof, aldehydes, ketones, carboxylic acids, carboxylic esters, carboxylic acid chlorides, carboxylic acid anhydrides, enones, nitriles, carbon dioxide, halogens, vinyl monomers, ring-opening monomers and combinations thereof.

26. The process of claim 21, further comprising:
exfoliating the functionalized graphene nanoribbons to form exfoliated, functionalized graphene nanoribbons.

27. The process of claim 21, further comprising:
oxidizing the functionalized graphene nanoribbons to form oxidized, functionalized graphene nanoribbons.

28. The process of claim 21, further comprising:
defunctionalizing the functionalized graphene nanoribbons to form defunctionalized graphene nanoribbons.

* * * * *